United States Patent
Varma et al.

(10) Patent No.: US 10,450,247 B2
(45) Date of Patent: Oct. 22, 2019

(54) METHOD OF PRODUCING HYDROCARBONS FROM METHANE

(71) Applicant: Purdue Research Foundation, West Lafayette, IN (US)

(72) Inventors: Arvind Varma, West Lafayette, IN (US); Yang Xiao, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 16/135,869

(22) Filed: Sep. 19, 2018

(65) Prior Publication Data

US 2019/0084904 A1 Mar. 21, 2019

Related U.S. Application Data

(60) Provisional application No. 62/560,692, filed on Sep. 20, 2017.

(51) Int. Cl.

| | |
|---|---|
| *C07C 9/06* | (2006.01) |
| *C07C 11/04* | (2006.01) |
| *C07C 2/00* | (2006.01) |
| *C01B 3/00* | (2006.01) |
| *C07C 2/76* | (2006.01) |

(52) U.S. Cl.
CPC .................. *C07C 9/06* (2013.01); *C01B 3/00* (2013.01); *C07C 2/00* (2013.01); *C07C 2/76* (2013.01); *C07C 11/04* (2013.01); *C07C 2521/18* (2013.01); *C07C 2523/644* (2013.01); *C07C 2529/44* (2013.01); *C07C 2529/48* (2013.01)

(58) Field of Classification Search
CPC ...... C10G 2300/104; C10G 2300/1044; C10G 2300/1096; C10G 2300/4018; C10G 2400/28; C10G 2400/30; C10G 35/085; C10G 35/09; C10G 35/095; C10G 47/18; C10G 49/06; C10G 49/08; C07C 9/04; C07C 2/66; C07C 2/76; C07C 2/78; C07C 2/08
See application file for complete search history.

(56) References Cited

U.S. PATENT DOCUMENTS 7,297,831 B2 * 11/2007 Lee .................. C10G 35/085
208/111.2

* cited by examiner

*Primary Examiner* — Sharon Pregler
(74) *Attorney, Agent, or Firm* — Purdue Research Foundation (57) ABSTRACT

A method for producing hydrocarbons and hydrogen from methane. The method includes packing a catalyst comprising platinum, bismuth and a support material into a reactor; introducing a reactant mixture containing methane into the reactor such that the reactant mixture containing methane is in close contact with the reactant mixture; and heating the reactant mixture containing methane to a temperature for a period of time.

14 Claims, 7 Drawing Sheets

METHOD OF PRODUCING HYDROCARBONS FROM METHANE

CROSS-REFERENCE TO RELATED APPLICATIONS

The present U.S. patent application is related to and claims the priority benefit of U.S. Provisional Patent Application Ser. No. 62/560,692 filed Sep. 20, 2017, the contents of which are hereby incorporated by reference in their entirety into the present disclosure.

TECHNICAL FIELD

The present application relates to production of hydrocarbons from methane through non-oxidative coupling of methane, in the presence of catalysts, especially bimetallic catalysts.

BACKGROUND

This section introduces aspects that may help facilitate a better understanding of the disclosure. Accordingly, these statements are to be read in this light and are not to be understood as admissions about what is or is not prior art. The abundance of methane, the main component of natural gas (~95%) and shale gas (typically >70%), on Earth makes it an attractive source for energy and chemicals for at least the next century. Catalytic transformation of methane to value-added chemicals plays an important role in methane utilization. Various routes have been considered, including indirect transformation which converts methane to syngas as intermediate followed by its further conversion to other compounds, and direct transformation which converts methane to higher hydrocarbons (e.g. ethylene, benzene) or oxygenates (e.g. methanol, formaldehyde) without any intermediate products. The direct transformation is more attractive because it saves both operating and capital costs. Among direct transformation technologies, oxidative coupling of methane (OCM) is promising because the primary products ($C_2$ species, ethane/ethylene) are precursors for a variety more high valuable products, e.g. plastics and resins. (The term coupling is well understood by chemists, chemical engineers and those skilled in the art. A coupling reaction in organic chemistry is a general term for a variety of reactions where two hydrocarbon fragments are coupled with the aid of a metal catalyst.) Tuning the selectivity towards $C_2$ species in OCM, however, has been a long-standing challenge since the 1980s, owing to the unavoidable presence of over-oxidized species ($CO/CO_2$) under oxidative conditions. (The term selectivity is well understood by those skilled in the art and generally refers to a measure of desired product formed in relation or ratio to all products—desired and undesired—formed. Other terms well understood include "conversion" which is a measure of the amount of the reactant that reacted, and "yield" which is a measure of the desired product formed in relation to the reactants. Hundreds of catalyst candidates have been prepared and tested for OCM, while carbon selectivity towards $CO/CO_2$ is typically about 50%, indicating uneconomic conversion of carbon atoms. Non-oxidative conversion of methane, first reported in 1993, improves carbon atom economy. Using Mo supported on zeolites, existing non-oxidative technologies generate benzene as the main product, but unavoidable coke formation limits catalyst lifetime and process commercialization. Although the selectivity toward benzene is typically about 80-90%, other aromatic hydrocarbons ($C_7$-$C_9$) as well as $C_2$ species (both ethane and ethylene) have also been reported. In a recent report, 2-3% methane conversion was reached over $Bi/SiO_2$ at 900° C. under non-oxidative conditions, while the selectivity toward $C_2$ products was about 40%.

Non-oxidative coupling of methane (NOCM) to form $C_2$ hydrocarbons has been considered since the 1990s. It has been reported that $C_2H_6$ and $H_2$ were immediately produced when $CH_4$ was fed continuously over a commercial 6% wt $Pt/SiO_2$ catalyst at low temperature 250° C., while owing to catalyst deactivation, both products disappeared for time on stream (TOS) more than 8 min. This indicates that methane can be activated at temperature lower than typically used in OCM (>700° C.). Other researchers showed that ethane with >98% carbon selectivity was produced over silica-supported tantalum hydride catalyst at temperature <500° C., although methane conversion was less than 0.5%. Others reported 48% conversion of methane under non-oxidative condition over $Fe/SiO_2$ catalyst at 950° C., producing ethylene, benzene and naphthalene with carbon selectivity of 53%, 22% and 25%, respectively. Some other researchers found similar products over Pt—Sn catalyst at 700° C.; however, the methane conversion was less than 0.3%.

As an important direct methane transformation technique, despite extensive research conducted for decades, oxidative coupling of methane (OCM) remains industrially uneconomic owing to low carbon selectivity (typically <50%) towards valuable target products ($C_2$ species, ethane/ethylene). Thus, there is an unmet need for methods and processes to produce $C_2$ hydrocarbons from methane in non-oxidative conditions with both high carbon selectivity and high conversion.

SUMMARY

A method for producing hydrocarbons and hydrogen from methane is disclosed. The method includes packing a catalyst comprising platinum, bismuth and a support material into a reactor; introducing a reactant mixture containing methane into the reactor such that the reactant mixture containing methane is in close contact with the reactant mixture; and heating the reactant mixture containing methane to a temperature for a period of time.

BRIEF DESCRIPTION OF DRAWINGS

Some of the figures shown herein may include dimensions. Further, some of the figures shown herein may have been created from scaled drawings or from photographs that are scalable. It is understood that such dimensions or the relative scaling within a figure are by way of example, and not to be construed as limiting.

DETAILED DESCRIPTION

For the purposes of promoting an understanding of the principles of the disclosure, reference will now be made to the embodiments illustrated in the drawings and specific language will be used to describe the same. It will nevertheless be understood that no limitation of the scope of the disclosure is thereby intended.

In this description, it is disclosed that the present disclosure describes that a catalyst containing platinum and bismuth supported on ZSM-5 zeolite selectively converts methane to ethane with high carbon selectivity (>90%) and typical methane conversion 2-3%, along with equivalent molar hydrogen generated as a by-product. The catalyst exhibits no deactivation for an 8-hour test, indicating good stability and prevention of coke formation. According to this disclosure, stable methane coupling is achieved in a continuous flow reactor, at relatively moderate temperatures (500-700° C.), with methane conversion >2% and carbon selectivity to $C_2$ hydrocarbon species >90%. In the context of this disclosure the terms "Pt—Bi catalyst" or "Pt—Bi bimetallic catalyst" mean platinum and bismuth supported on a support material such as but not limited to ZSM-5 zeolite.

In experiments leading to this disclosure, various Pt—Bi bimetallic catalysts were prepared, characterized and tested in a fixed-bed reactor. These catalysts exhibit similar BET surface area (372-412 m$^2$/g), pore size (2.8-3.5 nm), pore volume (0.33-0.41 cm$^3$/g) and Pt metal dispersion (22-29%). TEM scans showed that metals were successfully loaded on ZSM-5 support and the metal dispersion (calculated by TEM-based particle size) values were consistent with the $H_2O_2$ titration data. The XRD patterns for various Pt—Bi/ZSM-5 catalysts are compared to diffraction patterns for unsupported MFI/ZSM-5. (ZSM-5 (MFI) is well understood by those skilled in the art. Mobil-5 (framework type MFI from ZSM-5 (five)) is an aluminosilicate zeolite belonging to the pentasil family of zeolites. Its chemical formula is $Na_nAl_nSi_{96-n}O_{192}\cdot16H_2O(0<n<27)$ reported in the International Zeolite Association (IZA) structure database. Supported and unsupported ZSM-5 exhibit similar patterns, likely due to low metal loading (1 wt % or less) and high Pt dispersion (20-30%). The fresh and used catalysts contained essentially the same amount of Pt and Bi as designed.

As shown in FIG. 1, for the 1 wt % Pt catalyst, methane conversions were between 3% to 6%, while no hydrocarbon but only hydrogen was detected (FIG. 1A), owing to coke formation over the pure Pt surface. For the 1 wt % Bi catalyst, on the other hand, no methane conversion (<0.1%) was found. For the 1 wt % Pt-0.1 wt % Bi catalyst, methane conversion was similar to results of the 1 wt % Pt catalyst, with again no any hydrocarbon generated. For other four bimetallic catalysts with 1 wt % Pt and 0.1-1.0 wt % Bi, ethane was produced with a variety of carbon selectivity values ranging from 17% to 95%.

Figure 1A:
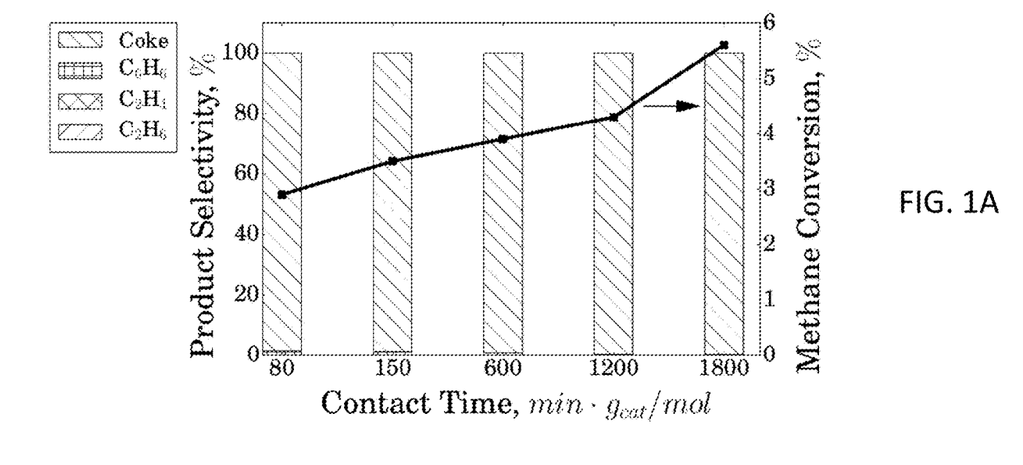
FIG. 1A shows Product Distribution at 650° C. and 0.1 atm Methane Partial Pressure over the 1% Pt/ZSM-5 Catalyst
Figure 1B:
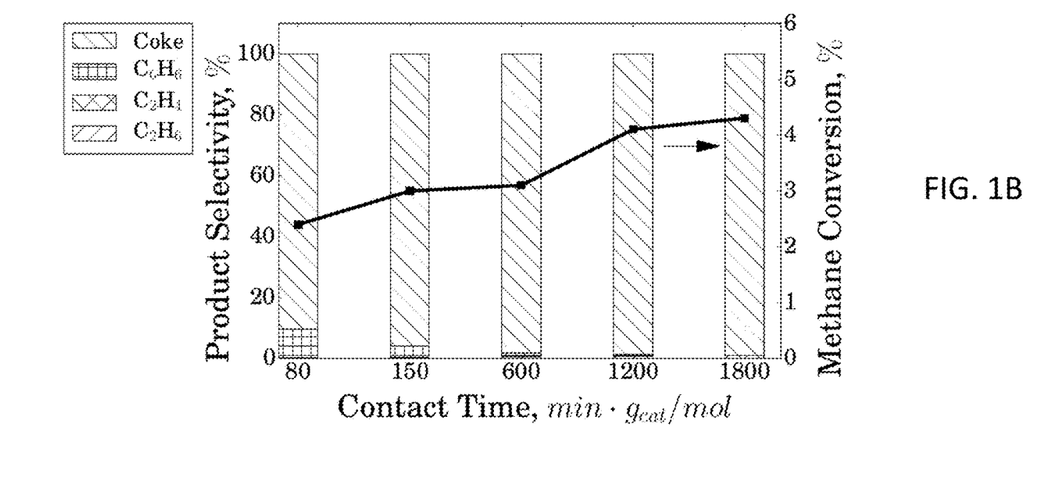
FIG. 1B shows Product Distribution at 650° C. and 0.1 atm Methane Partial Pressure over the 1% Pt-0.1% Bi/ZSM-5 Catalyst
Figure 1C:
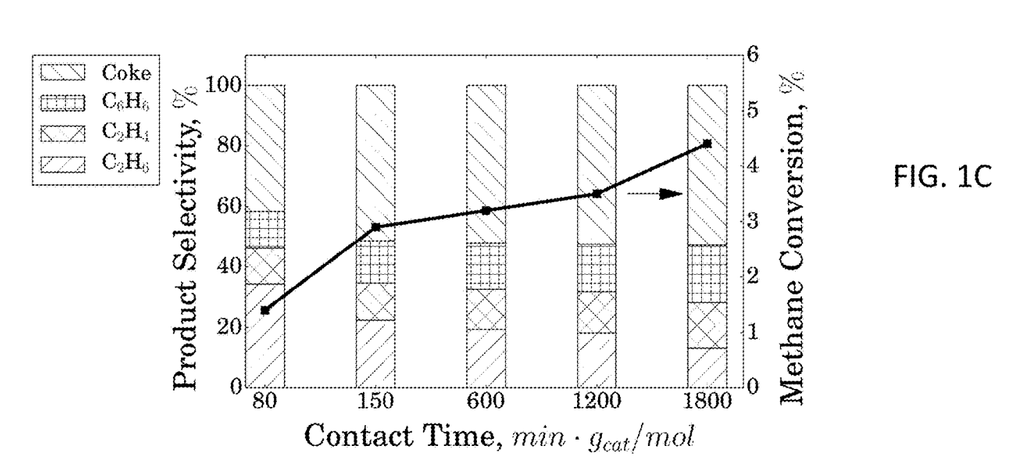
FIG. 1C shows Product Distribution at 650° C. and 0.1 atm Methane Partial Pressure over the 1% Pt-0.2% Bi/ZSM-5 Catalyst
Figure 1D:
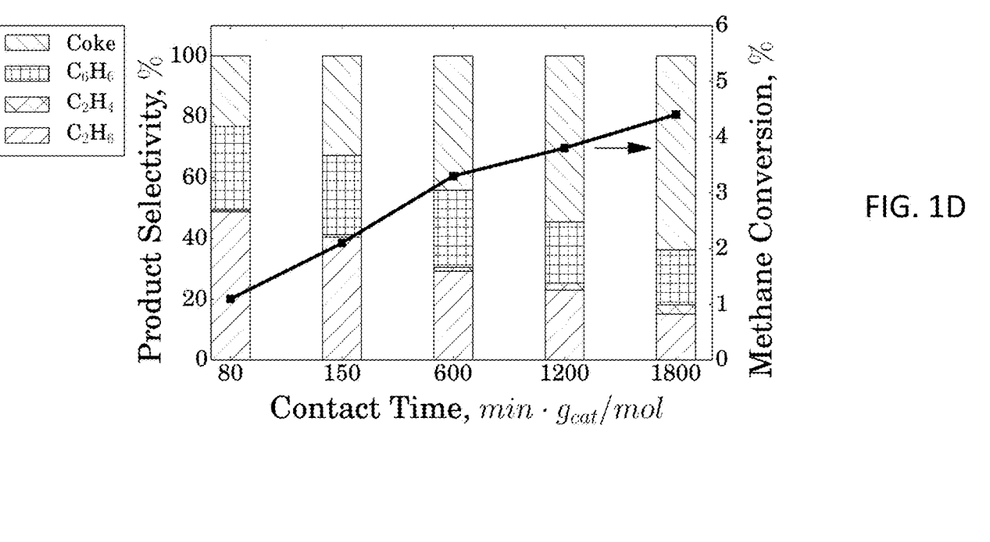
FIG. 1D shows Product Distribution at 650° C. and 0.1 atm Methane Partial Pressure over the 1% Pt-0.5% Bi/ZSM-5 Catalyst
Figure 1E:
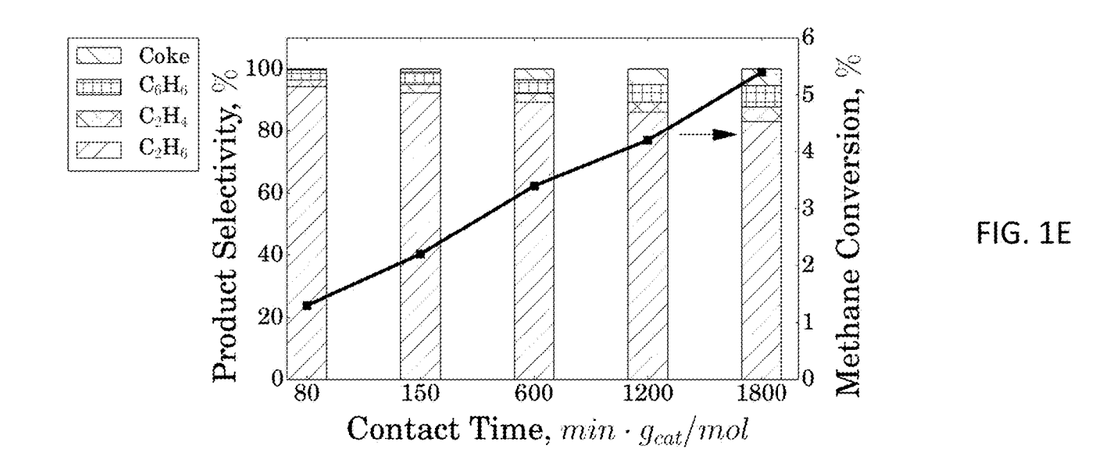
FIG. 1E shows Product Distribution at 650° C. and 0.1 atm Methane Partial Pressure over the 1% Pt-0.8% Bi/ZSM-5 Catalyst
Figure 1F:
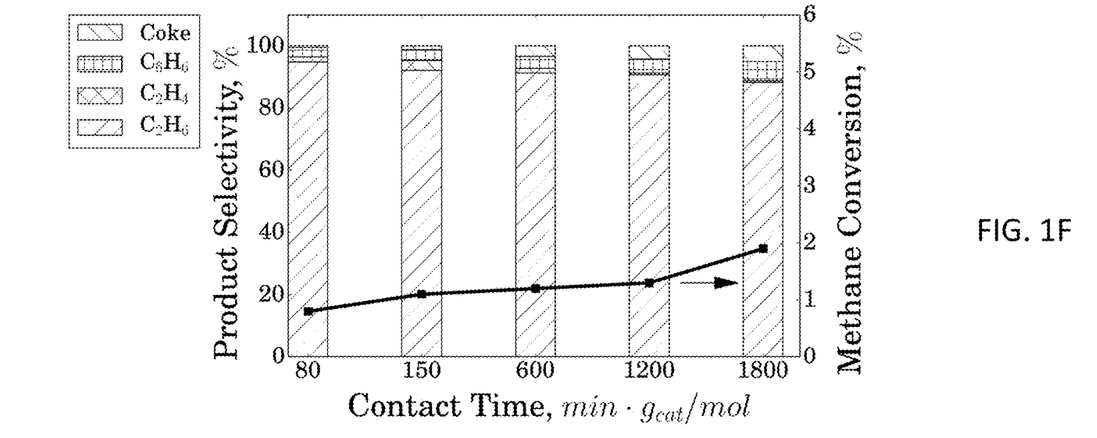
FIG. 1F shows Product Distribution at 650° C. and 0.1 atm Methane Partial Pressure over the 1% Pt-1% Bi Catalyst
Figure 2A:
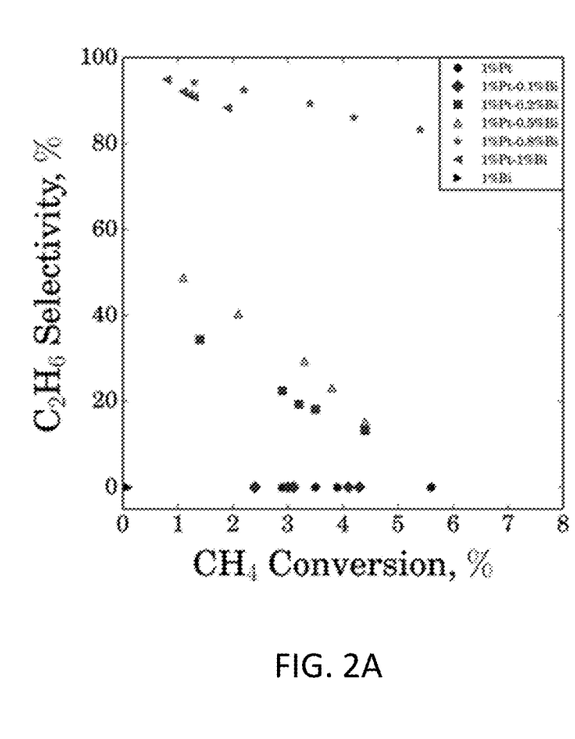
FIG. 2A shows Ethane Selectivity for Different Pt—Bi/ZSM-5 Catalysts under Various Methane Conversions, at 650° C. and 0.1 atm Methane Partial Pressure.

FIG. 2A shows ethane selectivity for different Pt—Bi/ZSM-5 catalysts under various methane conversions, at 650° C. and 0.1 atm methane partial pressure. Referring to FIG. 2A, it can be seen that by varying contact time of feed methane with packed catalyst, different methane conversions were obtained. (Unit of Contact Time (t) is obtained as follows:

F (Species flowrate): mol/min
W (Catalyst packing amount): $g_{cat}$
Definition of contact time:
t=W/F=($g_{cat}$)/(mol/min)=min·$g_{cat}$/mol All methane conversions were less than 7%, limited by thermodynamic equilibrium under the operating conditions, corresponding to $$CH_4 \rightarrow 0.5C_2H_6 + 0.5H_2 \qquad (1)$$

$$CH_4 \rightarrow 0.5C_2H_4 + H_2 \qquad (2)$$

As shown in FIG. 2A, the carbon selectivity toward ethane always decreased with increase of methane conversion for all four catalysts. In particular, for the 1 wt % Pt-0.8 wt % Bi catalyst, carbon selectivity towards ethane was 85-95% when methane conversion was 1-5%. Note that equilibrium methane nonoxidative conversion to $C_2$ species is about 2-3% at 650° C., while higher than equilibrium conversion was typically observed for methane nonoxidative conversion at short time on stream (TOS) in the literature. For consistency, all data reported in our work for catalytic performance comparison were taken at 1 h TOS. As reported in the literature, Bi addition to Pt could tune catalytic activity, where Bi functions as site blocker [28,29], while Bi alone shows poor catalytic activity. For increasing amounts of Bi addition to Pt, chemisorption of small molecules (e.g., $H_2$, CO, and $C_2H_4$) was found to be attenuated, indicating relatively lower activity for reaction and higher tolerance for poison species. Coverage values of chemisorbed species, influenced by both geometric and electronic effects, also depend on molecular size, which indicates that, for a specific reaction, a particular Pt/Bi composition is favored. For example, it was reported that $Pt_{1.00}Bi_{0.95}$ exhibits excellent activity for hydrogen evolution, while prior work described that 3% Pt-0.6% Bi provides the highest 1,3-dihydroxyacetone yield from glycerol selective oxidation.

Figure 2B:
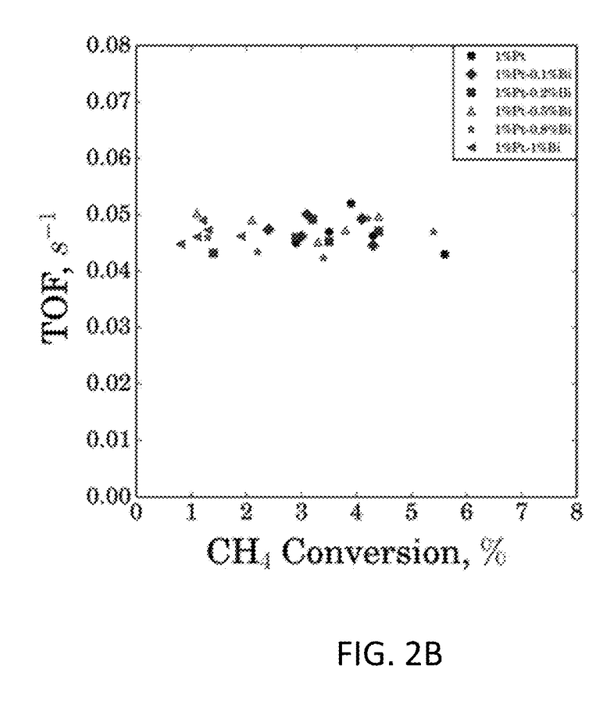
FIG. 2B shows Turnover Frequency (TOF) for Different Pt—Bi/ZSM-5 Catalysts under Various Methane Conversions, at 650° C. and 0.1 atm Methane Partial Pressure.

FIG. 2B shows turnover frequency (TOF) for different Pt—Bi/ZSM-5 catalysts under various methane conversions, at 650° C. and 0.1 atm Methane Partial Pressure. Referring to FIG. 2B it can be seen that that over various catalysts tested in FIG. 2A, turnover frequencies (TOF) based on Pt surface dispersion were essentially constant (0.042-0.053 s$^{-1}$). This feature demonstrates that surface Pt is the active site for methane activation, as reported previously in literature.

Figure 3A:
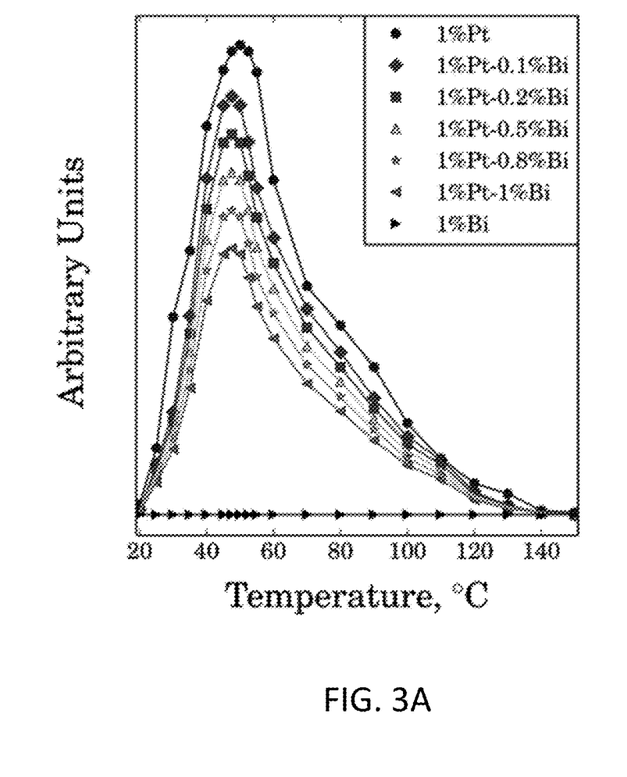
FIG. 3A shows a Temperature-Programmed Investigation showing $H_2$ Desorption ($H_2$-TPD) from Different Pt—Bi/ZSM-5 Catalysts 0.1 atm Methane Partial Pressure and 600 min·$g_{cat}$/mol Contact Time.
Figure 3B:
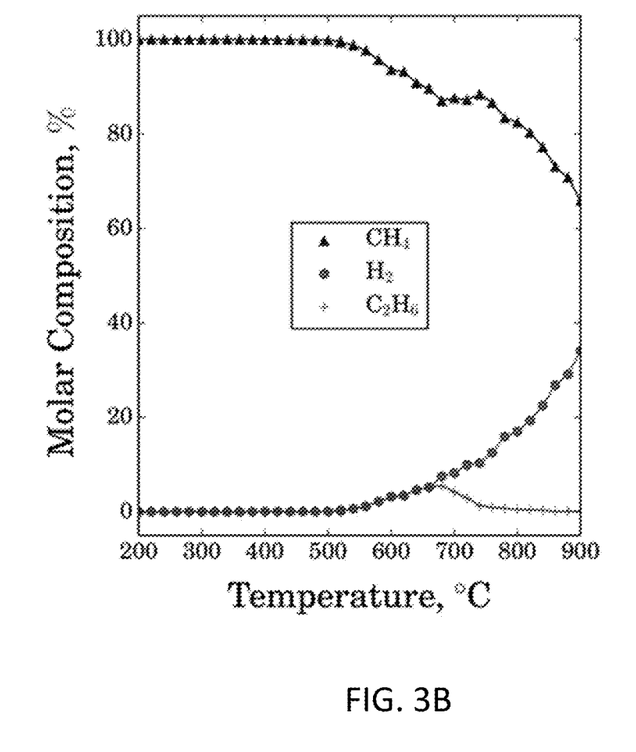
FIG. 3B shows another Temperature-Programmed Investigation showing Surface Reaction (TPSR) Profiles for 1% Pt-0.8% Bi/ZSM-5 Catalyst at 0.1 atm Methane Partial Pressure and 600 min·$g_{cat}$/mol Contact Time.

FIG. 3A shows $H_2$ temperature-programmed desorption ($H_2$-TPD). Profiles in FIG. 3A demonstrate that hydrogen uptake at room temperature was attenuated with increasing Bi addition to Pt/ZSM-5. Bi has been reported to function as a site blocker onto Pt surface, hence less activity of the Pt—Bi bimetallic catalysts. For 1 wt % Bi catalyst, no hydrogen uptake was found, indicating inactive nature for Bi as shown in FIG. 2 A. Temperature-programmed surface reaction (TPSR) profiles in FIG. 3B describe that below 500° C. methane cannot be activated, owing to chemical stability of methane molecule. Between ca. 500 to 650° C., methane was converted to equivalent molar amounts of ethane and hydrogen, as indicated by reaction: Eq. (1). From ca. 700 to 800° C., methane conversion continued to increase, while ethane concentration decreased from ca. 2.5% to nearly zero. Hydrogen production rate from 700 to 900° C., however, continued to increase, implying further dehydrogenation of methane and leading to coke formation. As reported in the literature, not only initial activation of methane ($CH_4 \rightarrow CH_3 + H$), but also further dehydrogenation of methane (e.g. forming $CH_2$, CH and C species) occurs over Pt surface owing to relatively low reaction barriers of C—H bond cleavage (<1 eV). Thus as compared to C—C coupling (reaction barriers typically >2 eV over flat surface and 1-2 eV over step surface), Pt catalysts preferably promote further dehydrogenation of methane rather than C—C coupling, eventually forming coke, which is consistent with the 1 wt % Pt curve in FIG. 2A. In addition to the Pt surface, C—C coupling could also occur at acidic sites of ZSM-5, as reported previously. Since the 1% Pt/ZSM-5 catalyst, as described in FIGS. 1 and 2, did not lead to any $C_2$ product, the acidic site in ZSM-5 appears to be inactive for C—C coupling in NOCM conversion in the present study. Ethane dehydrogenation to ethylene and/or acetylene could occur over pure Pt surfaces. With the addition of a second metal to Pt, binding of molecules is typically weaker over bimetallic surfaces, indicating relatively higher reaction barriers. As reported in the literature, a shorter contact time favors lower reactivity of ethane dehydrogenation. These are likely reasons for the limited ethane dehydrogenation product in the present study. By adding Bi to Pt/ZSM-5 catalyst, as reported in FIGS. 2A and 3B, methane was activated under relatively low temperature (500-700° C.), while further dehydrogenation of methane, leading to coke deposit, were suppressed owing to the less active Pt—Bi surface as compared to pure Pt surface.

Temperature-programmed oxidation (TPO) investigations for used 1% Pt and used 1% Pt-0.8% Bi catalysts show that initial oxidation of used 1% Pt occurred at ca. 300° C., followed by two clear peaks at 440 and 540° C., respectively. For used 1% Pt-0.8% Bi, however, only one distinguished peak was identified, although it was followed by slight dragging (indicating another small peak). By integrating TPO curves, accumulated coke amounts were obtained. The 1% Pt-0.8% Bi after deployment as a catalyst contained much less coke (27 mg/$g_{cat}$) than the used 1% Pt (497 mg/$g_{cat}$). These observations suggest that by addition of Bi to Pt/ZSM-5 catalyst, methane was activated at relatively low temperature (600-700° C.), while further dehydrogenation of methane, leading to coke deposits, was suppressed owing to the less active Pt—Bi surface in comparison to the pure Pt surface. In our prior works, Bi was used as a promoter for either tuning selectivity toward target products or improving catalyst stability. With the participation of guaiacol molecules over Pt—Bi catalysts, it was proposed that $CH_4$ partially decomposed on the Pt surface and methyls coupled to form ethane. It appears that, in the present work, Bi addition to Pt combines these two functions: promoting NOCM selectivity to ethane and extending catalyst lifetime.

Figure 4A:
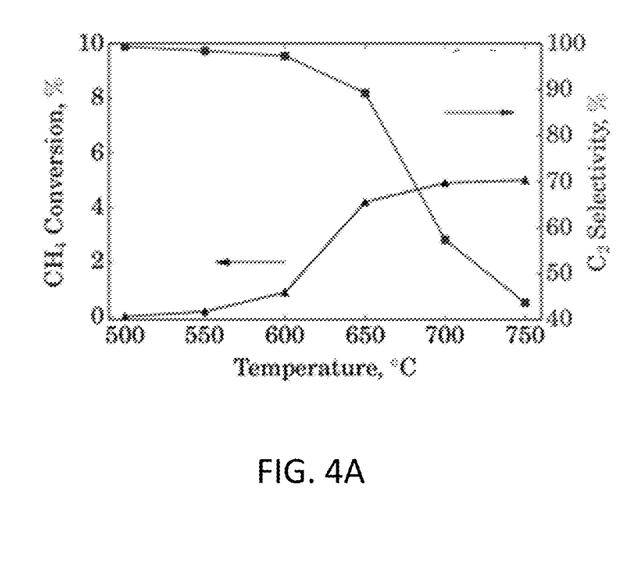
FIG. 4A shows Effect of Temperature on Conversion and Selectivity at 0.1 atm Methane Partial Pressure and 600 min·$g_{cat}$/mol Contact Time.
Figure 4B:
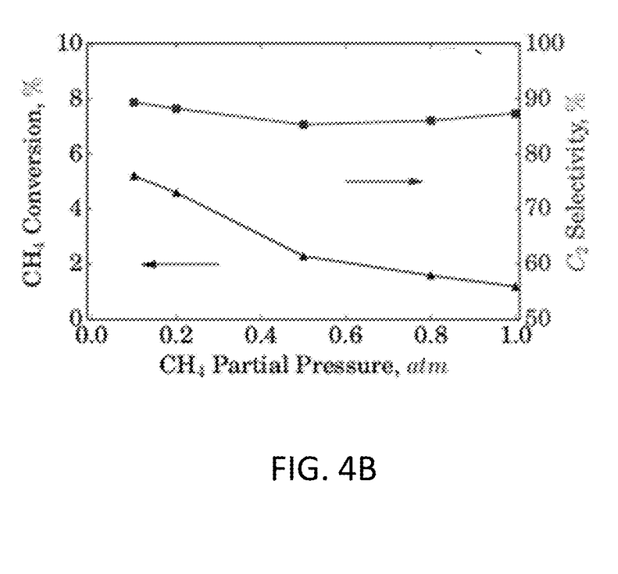
FIG. 4B shows Effect of Methane Partial Pressure on Conversion and Selectivity at 650° C. and 600 min·$g_{cat}$/mol Contact Time.
Figure 4C:
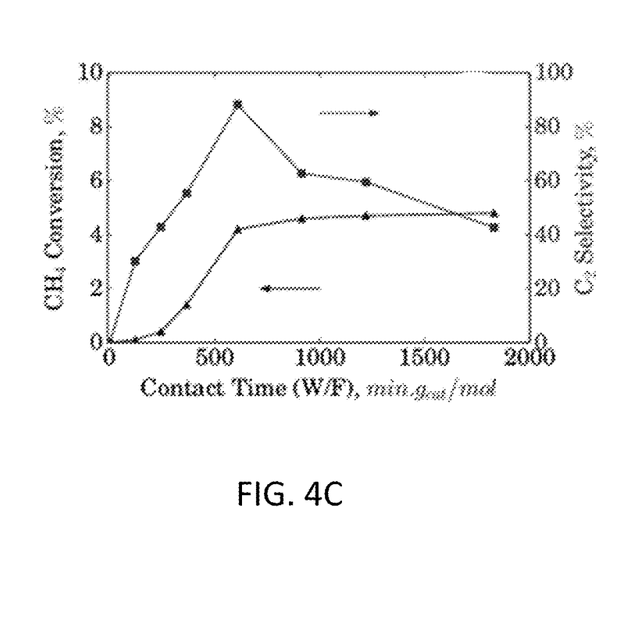
FIG. 4C shows Effect of Contact Time on Conversion and selectivity at 0.1 atm Methane Partial Pressure and 650° C.
Figure 4D:
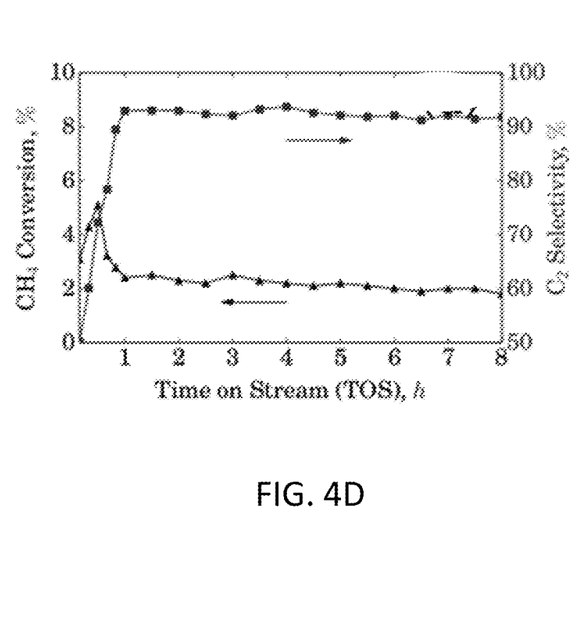
FIG. 4D shows Effect of Catalyst Stability on Conversion and Selectivity at 0.1 atm Methane Partial Pressure, 650° C. and 300 min·$g_{cat}$/mol Contact Time.

FIG. 4A shows temperature effect on NOCM over the range 500-700° C. Similar to results shown in FIG. 3B, methane conversion increased with temperature while ethane selectivity decreased, reaching maximum ethane yield (selectivity×conversion) 1.8% at 650° C. For standard operating conditions, methane partial pressure was 0.1 atm. FIG. 4B shows that 0.1-1 atm of methane partial pressure gave essentially the same $C_2$ selectivity, yet higher methane conversion at lower methane partial pressure. This feature occurs when thermodynamics dominates NOCM conversion. FIG. 4C illustrates the contact time effect on NOCM conversion. When long contact time was used, the main by-product was aromatic coke, although small amounts of ethylene and benzene were detected as well. It has been proposed that in all non-oxidative conversion of methane, $C_2$ species was produced as intermediates for either heavier hydrocarbon or coke formation. Thus methane conversion typically follows a series reaction network: $CH_4 \rightarrow C_2H_6 \rightarrow C_xH_y$ (x>2, y≥0). In the present disclosure, since the intermediate $C_2$ species was the target product, as shown in FIG. 4C, it exhibited a selectivity peak at ca. 600 min·$g_{cat}$/mol, as expected from kinetic analysis. FIG. 4D shows that, following an initial transient period, both methane conversion and carbon selectivity towards ethane were stable over the entire 8-hour test.

From the foregoing discussion, it can be seen that, in general, existing technologies for direct transformation of methane are not followed industrially owing to inefficient carbon atom utilization. In the present disclosure a simple heterogeneous catalytic process is described which can be carried out under relatively moderate temperature (500-700° C.) for stable methane conversion into ethane with carbon selectivity >90% and methane conversion 2-3%. With incorporation of available separation and recycling schemes, the technology of this disclosure can be exploited on an industrial scale.

From the foregoing detailed description, it is an objective of this disclosure to describe a method for producing hydrocarbons and hydrogen from methane. The method includes packing or placing a catalyst comprising Pt (primary metal), Bi (promoter) and a support for platinum/bismuth into a reactor, and introducing a reactant mixture containing methane into the reactor in which the catalyst is placed such that the reactant mixture comes into contact with the catalyst. Such packing or placing the catalyst in the rector is generally well understood by those skilled in the art. The reactant mixture containing methane is then heated to a temperature for a "contact time". The phrase contact time is well understood by those skilled in chemical engineering processes and typical units for contact time are min.$g_{cat}$/mol , as explained earlier (mol=mole).

It should be noted that some embodiments of the methods of this disclosure, the reactor is a tubular reactor.

A non-limiting range of the temperature to which is the reactant mixture is heated in the reactor is in the non-limiting range of 473 K-1273 K. The contact time for the methane feed form the reactant mixture is in the non-limiting range of 50-1500 min.gcat/mol. A non-limiting range for the partial pressure of methane in the reactant mixture is 0.1 to 1.0 atmosphere. In one version of the method, the reactant mixture does not contain any oxygen. In some versions of the method, the reactant mixture can include an inert gas such as, but not limited to argon or helium or nitrogen or a combination thereof.

Methods of using support materials are well known to those skilled in the art and are well described in literature. A non-limiting range for particles comprising such a support material is 200 mesh to 10 mesh. Examples of such support materials suitable for the methods of this disclosure include but not limited to activated carbon and ZSM-5 zeolite. If activated carbon is used as a support material, a non-limiting range for the specific surface area of the activated carbon is 200-2000 $m^2/g$. If ZSM-5 zeolite is used as a support material, a non-limiting range for the specific surface area of the ZSM-5 zeolite is 100-800 $m^2/g$. Further, a non-limiting range for Si/Al ratio of ZSM-5 zeolite for use a support material for the catalysts of this disclosure is 22 to 250.

The platinum loading in the "platinum-bismuth-support material" combination is in the non-limiting range of 0.1 to 5.0 weight percent. The bismuth loading in the "platinum-bismuth-support material" combination is in the non-limiting range of 0.1 to 5.0 weight percent. An example of such loading is 2% Pt-3% Bi-95% ZSM-5.

While the present disclosure has been described with reference to certain embodiments, it will be apparent to those of ordinary skill in the art that other embodiments and implementations are possible that are within the scope of the present disclosure without departing from the spirit and scope of the present disclosure. Thus, the implementations should not be limited to the particular limitations described. Other implementations may be possible.

The invention claimed is:

1. A method for producing hydrocarbons and hydrogen from methane comprising:
    packing a catalyst comprising platinum, bismuth and a support material into a reactor;
    introducing a reactant mixture containing methane and an inert gas into the reactor; and
    subjecting the reactant mixture to a methane coupling reaction to produce hydrocarbons comprising ethane, the coupling reaction comprising a temperature between 500 C. to 700 C. and a time between 1 and 8 h,
    wherein the reactant mixture containing methane is converted to ethane with a carbon selectivity of at least 90%.

2. The method of claim 1, wherein the contact time is in the range of 50-1500 $min.g_{cat}/mol$.

3. The method of claim 1, wherein the partial pressure of methane in the reactant mixture is in the range 0.1-1.0 atmosphere.

4. The method of claim 1, wherein the reactant mixture does not contain oxygen.

5. The method of claim 1, wherein the inert gas is one of argon, helium and nitrogen.

6. The method of claim 1, wherein platinum loading in the catalyst is in the range of 0.1-5.0 weight %.

7. The method of claim 1, wherein bismuth loading in the catalyst is in the range of 0.1-5.0 weight %.

8. The method of claim 1, wherein the support material is activated carbon.

9. The method of claim 8, wherein the specific surface area of the activated carbon is in the range of 200-2000 $m^2/g$.

10. The method of claim 1, wherein the support material is ZSM-5 zeolite.

11. The method of claim 10, wherein the specific surface area of the ZSM-5 zeolite is in the range of 100-800 $m^2/g$.

12. The method of claim 1, wherein the particle size of the support material is from 200 mesh to 10 mesh.

13. The method of claim 10, wherein the Si/Al ratio of ZSM-5 zeolite support is from 22 to 250.

14. The method of claim 1, the reactor is a tubular reactor.

* * * * *